United States Patent [19]

Herrera

[11] Patent Number: 5,032,082

[45] Date of Patent: Jul. 16, 1991

[54] DEVICE FOR REMOVING ADHESIVE FROM THE PALATE

[76] Inventor: William R. Herrera, 600 North A St., Oxnard, Calif. 93030

[21] Appl. No.: 452,615

[22] Filed: Dec. 20, 1989

[51] Int. Cl.$^5$ .................. A61C 3/00; A61C 3/06; A46B 9/04; A61H 7/00

[52] U.S. Cl. .................. 433/141; 433/142; 15/167.1; 128/62 A

[58] Field of Search .......... 433/141, 142, 229; 15/167.1; 128/62 A, 62 R

[56] References Cited

U.S. PATENT DOCUMENTS

| | | | |
|---|---|---|---|
| 42,119 | 1/1912 | Thompson | 128/62 R |
| 1,153,409 | 9/1915 | Wheeler . | |
| 1,993,662 | 3/1935 | Green | 15/110 |
| 2,083,595 | 6/1937 | Clarren | 128/62 |
| 2,103,083 | 3/1936 | Lynch | 128/62 A |
| 2,129,082 | 9/1938 | Byrer . | |
| 2,206,726 | 7/1940 | Lasater . | |
| 4,081,877 | 4/1978 | Vitale | 15/188 |
| 4,128,910 | 12/1978 | Nakata et al. | 15/110 |
| 4,229,208 | 11/1981 | Blac | 128/62 |

FOREIGN PATENT DOCUMENTS 909768 7/1949 Fed. Rep. of Germany ... 128/62 A

Primary Examiner—John J. Wilson
Assistant Examiner—Cindy A. Cherichetti
Attorney, Agent, or Firm—George J. Netter

[57] ABSTRACT

A denture adhesive removing head is affixed to one end of an elongated handle. The head has several lines of projections extending from a common surface. The outer ends of the projections lie on a convexly curved surface. The head and projections are molded from a material that is pliable when warm and relatively rigid when cooled.

7 Claims, 2 Drawing Sheets

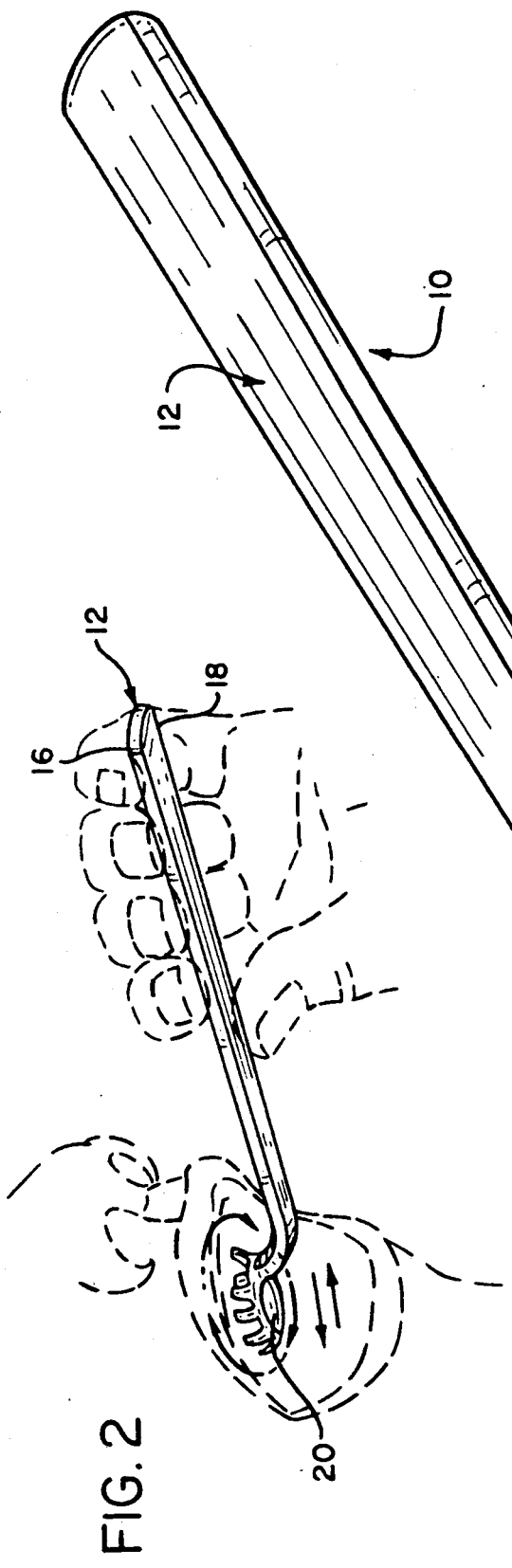
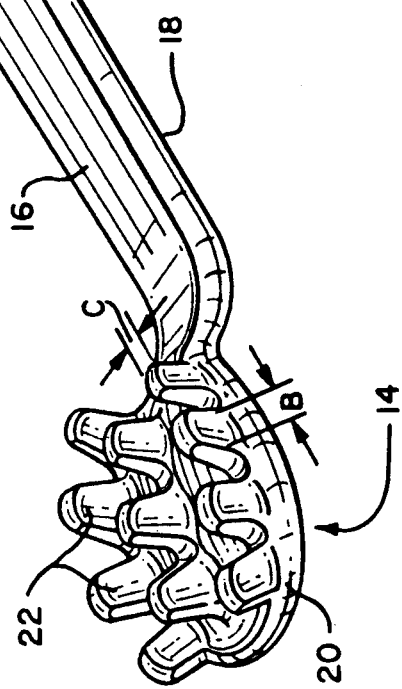

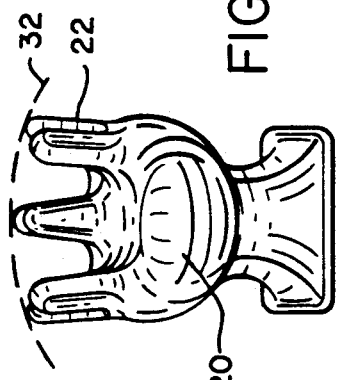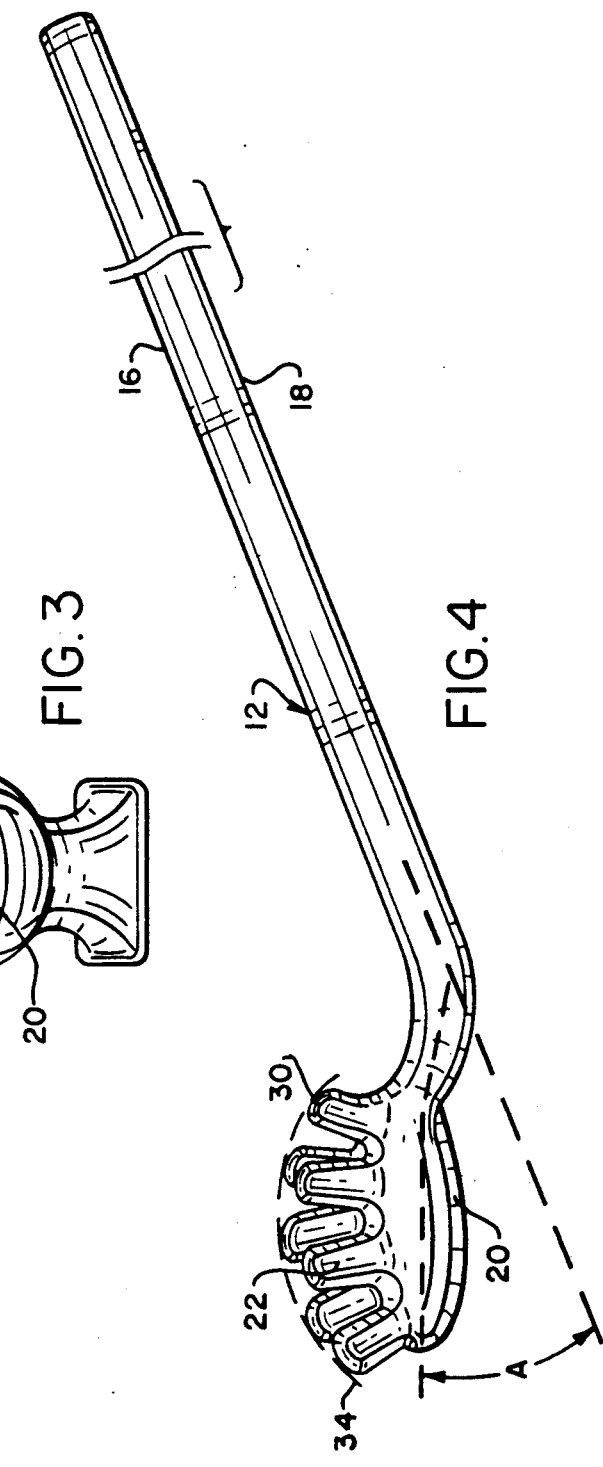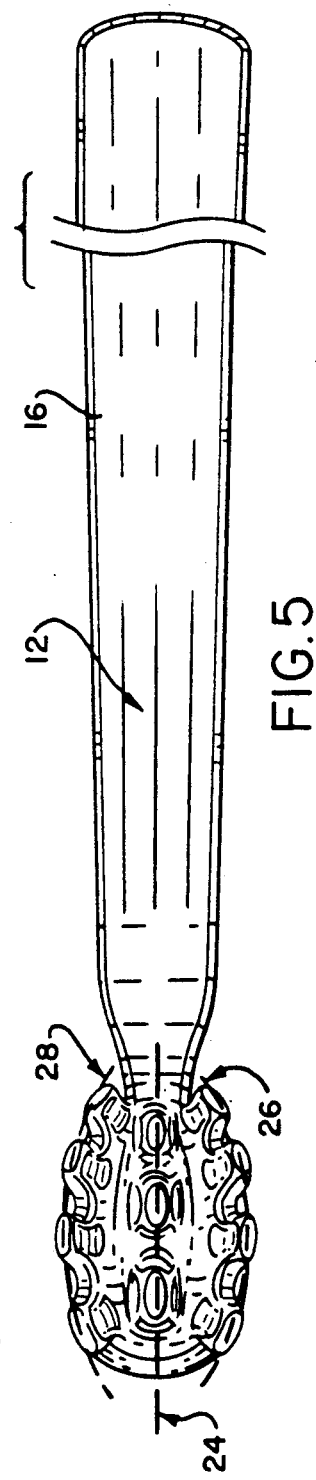

DEVICE FOR REMOVING ADHESIVE FROM THE PALATE

BACKGROUND OF THE INVENTION

1. Field of the Invention

The present invention relates generally to a device for removing accumulated denture adhesive from the palate and associated denture. Additionally, the described device is adaptable for cleaning all mouth tissues including gum areas.

2. Description of Related Art

It is common experience among denture wearers to have to use an adhesive or cement for securing the dentures in place to accommodate mouth structural changes which have occurred causing the denture to be less than a precise fit. There is a common tendency for the adhesive to accumulate on the hard palate of the individual and adjacent tissue areas which is not only uncomfortable, but also promotes bad breath and produces distasteful saliva. Still further, the adhesive frequently remains fixed even to removed dentures.

In the past, removal of adhesive accumulations from the palate has been on a makeshift basis in which the individual would use whatever was conveniently at hand. For example, the most probable device used for this purpose is a bristle brush of some kind such as a conventional toothbrush. However, a bristle brush is grossly inadequate in that the adhesive, once it has set up, is a rather hard substance requiring more force than can be safely obtained and applied by a bristle brush. For example, applying sufficient pressure with bristle brush to remove the adhesive poses a risk of damaging the adjacent tissues, scratching or causing them to bleed, which is obviously undesirable. If a soft bristle brush is utilized, it may be too soft to be even moderately effective for removing the adhesive.

Although a great variety of toothbrushes are available at the present time, and, as well, possibly a number of devices for stimulating and massaging the gums and mouth tissues, none of these are known to be contemplated for removing denture adhesive from the palate and dentures, nor are any of them believed to be satisfactory for this purpose.

SUMMARY OF THE INVENTION

The device of the present invention includes an elongated handle adapted for gripping primarily in the fingers of one hand. One end of the handle includes an adhesive removing head portion extending at a substantial angle from the handle longitudinal axis. Three sets of projections extend from the same surface of the adhesive removing head and are arranged in separate lines. More particularly, a first or central set of projections lies in a plane passing through the handle axis with the top ends of the projections lying in a convexly curved path. The other two sets of projections are arranged at each side of the first described central set, and are formed to lie in respective lines curved concavely toward the central set. The outer ends of the projections of the side sets do not extend outwardly as much as those of the central line resulting in all of the projection ends or tips lying in a convexly curved surface facing away from the head.

The individual projections are identically formed except for length. More particularly, each projection has a width dimension measured along the line of the set within which it resides that is several times that of the thickness dimension measured transversely thereto.

The projections on the adhesive removing head are constructed of a synthetic plastic material which has selectively controllable pliability. More particularly, the material is such that when it is immersed in hot water (or otherwise heated) it will become relatively soft and pliable, but if placed in cold water it will become rigid and substantially less pliable. This permits a self-adjustment by the user to conform to a particular adhesive removing operation. For example, if there is a stubborn accrual of adhesive on a portion of the palate or denture, the adhesive removal head can be inserted in cold water making the projections stiffer, and, therefore, better for removing the hard adhesive. On the other hand, if there is only a relatively loosely secured quantity of adhesive on the palate, or the palate in the region of the adhesive is sensitive, then the device head can be inserted in warm or hot water making the projections softer to the touch and less liable to irritate the palate and surrounding tissues. Projection material flexibility also allows maximum cleaning coverage of the denture itself.

DESCRIPTION OF THE DRAWINGS

In the accompanying drawings:

FIG. 1 is a perspective view of the adhesive removing device of the present invention;

FIG. 2 is a side elevational, schematic view showing the device in use;

FIG. 3 is an end elevational view of the adhesive removal head;

FIG. 4 is a side elevational view showing curvature of the device; and

FIG. 5 is a top plan view of the device.

DESCRIPTION OF A PREFERRED EMBODIMENT

Turning now to the drawings, and, particularly FIG. 1, the device of the present invention is enumerated generally as 10 and includes in its major parts an elongated handle 12 and an adhesive removing head 14 which is integrally connected to the handle. The handle 12 is contemplated for being held primarily in the fingers, and includes an upper flat surface 16 on which the fingers can exert pressure with the lower surface 18 parallel to the upper surface against which the thumb presses in use. As will be more particularly described, it is believed that the average user of the device will find this the most convenient way of manipulating the device to remove adhesive from the palate.

As can be best seen in FIGS. 2 and 4, the adhesive removing head 14 has a platelike base 20 which is canted with respect to the handle 12 at a substantial angle A, preferably about 30 degrees, so that the upper or active surfaces of the head to be described are suitably oriented for contacting the palate, which is a generally more or less sharply concave surface in the upper region of the mouth cavity just behind the teeth. With the angular orientation of the head noted, the cleaning portions of the head can be easily brought into contact with all of the palate surfaces while maintaining the handle in a position extending substantially straight forward out of the mouth, and, therefore, not requiring holding the handle at an awkward angle which would make manipulation difficult.

Turning again to FIG. 1 and FIG. 5 as well, the head 14 is seen to include a plurality of pressure applying projections 22 arranged in three separate lines 24, 26 and 28, all generally extending along the same direction as the handle 12. More particularly, a first or central line of projections 24 consists of three such projections 22 arranged in a straight line and lying in a single plane that is substantially normal to the handle upper surface 16. The two other lines of projections (26, 28) lie, respectively, at each side of the central line 24 and are curved convexly outwardly from the central line. Each of the projection lines 26 and 28 is defined by preferably four equispaced projections.

The projections 22 are preferably unitarily molded with the base 20 with the projections being identically shaped except for height as will be described. Specifically, each projection has a width B measured along the line (24, 26, 28) within which it is located that is several times greater than its thickness C. Also, each projection has an outer tip 30 that is rounded forming an outer end surface free from corners or edges which could tear or irritate the palate.

The various projections 22 extend at different heights from the base 20 such that the tips lie on a surface which is convexly curved both when viewed along a line axis as shown in FIG. 3 at 32 and when viewed from the side as in FIG. 4. By this arrangement of outer end surfaces of the projections, a multi-point pressure exerting surface is provided which very closely fits within the palate of an average individual. True, the palates of individual users will vary in size, however, the collective shape that is specially provided for the projection outer end tips enables fitting receipt into the palate region and enables ready adhesive removal action on all of the palate surfaces and adjacent tissues. Although some variation in size can be tolerated, best results to date have been achieved with the projection tips forming a convex surface measuring approximately ¾ inches long and having a maximum width of approximately ½ an inch.

The adhesive removing head 14 and each of the projections 28 thereof are preferably molded from a material which can be selectively made harder or softer to the touch, as desired in use. For example, there are plastics on the open market for making the head and projections which when immersed in hot water (or otherwise heated) will become relatively pliant. Alternatively, if a head made from these plastics is cooled by immersing in cold water, for example, the projections would become relatively rigid. An example of such a material which would be satisfactory for the present use is a material known as a heat cure soft reline acrylic manufactured and sold by PRO-TECH of Centereach, N.Y.

To use the device 10, it is clasped primarily in the fingers with the thumb pressed against the handle lower surface 18 and the remaining fingers pressing against the handle top flat surface 16. Now, the head 14 is inserted into the mouth as shown in FIG. 2 and the device is reciprocated to remove adhesive that has accumulated on the palate (parallel arrows) and/or moved in a circular path (arrows). When through, the device merely requires rinsing to clean it.

Not infrequently, adhesive clings to the denture and must be removed after the denture is taken from the mouth. Although the described device is primarily contemplated for removing adhesive from the palate and adjacent tissue, it can be readily adapted for removing adhesive from the denture itself.

Although the present invention has been described in connection with a preferred embodiment, it is to be understood that one skilled in the art can suggest changes in form, construction and materials which would, nevertheless, come within the spirit of the invention and the scope of the appended claims.

What is claimed is:

1. A device for removing denture adhesive from the palate and adjacent tissues, comprising:
   a handle;
   a base integrally related to the handle; and
   a plurality of separate spaced apart projections extending from the base in the same general direction, each projection having a width at least several times its thickness and a tip which is rounded and free of sharp corners and edges, said tips collectively lying on a single outwardly directed convexly curved surface said surface being curved in two planes transverse to each other;
   said base and projection being molded from a synthetic plastic the pliability of which is increased with temperature increase and decreased by temperature decrease.

2. A device as in claim 1, in which the projections are arranged in a first straight line, and second and third lines respectively at each side of the first line, said second and third lines being curved concavely toward the first line.

3. A device as in claim 2, in which the base extends upwardly away from the handle at an angle of approximately 30 degrees to the handle axis.

4. A device as in claim 1, in which the convexly curved surface is approximately ¾ inches long by ½ inch wide.

5. A device for removing denture adhesive from the palate and other mouth tissues, comprising:
   a handle;
   a base unitarily with the handle;
   a plurality of separate spaced apart projections extending from the base, each projection having a width measured generally parallel to the longitudinal axis of the handle at least twice its thickness measured transversely of the width and a tip which is rounded and free of sharp corners and edges, said tips collectively lying in a single convexly curved surface; and
   said projections being arranged in a first straight line, and second and third lines respectively arranged at each side of the first line, and being curved concavely toward the first line.

6. A device as in claim 5, in which the convexly curved surface is curved about two axes normal to each other.

7. A device as in claim 6, in which the base and projections are integrally molded from a synthetic plastic the pliability of which is increased by contact with hot tap water and decreased by contact with cold tap water.

* * * * *